United States Patent [19]

Kumar et al.

[11] Patent Number: 5,917,058

[45] Date of Patent: Jun. 29, 1999

[54] PROCESS OF LACTONIZATION IN THE PREPARATION OF STATINS

[75] Inventors: Yatendra Kumar; Rajesh Kumar Thaper, both of Haryana; S. M. Dileep Kumar, New Delhi; Jag Mohan Khanna, Haryana, all of India

[73] Assignee: Ranbaxy Laboratories Limited, New Delhi, India

[21] Appl. No.: 09/064,285

[22] Filed: Apr. 22, 1998

[30] Foreign Application Priority Data

Oct. 28, 1997 [IN] India ............................... 3102/DEL/97

[51] Int. Cl.$^6$ .................................................. C07D 309/30

[52] U.S. Cl. ............................................................. 549/292

[58] Field of Search .............................................. 549/292

[56] References Cited

U.S. PATENT DOCUMENTS 4,820,850  4/1989  Verhoeven et al. ..................... 549/292
4,916,239  4/1990  Treiber ..................................... 549/292

*Primary Examiner*—Amelia Owens
*Attorney, Agent, or Firm*—Jayadeep R. Deshmukh

[57] ABSTRACT

An improved process of lactonization in the preparation of statins (e.g., the HMG—CoA reductase inhibitors lovastatin and simvastatin) employs very mild reaction conditions. The improved process comprises treating the open ring hydroxy acid form of the statins with an excess of acetic acid and in the absence of a strong acid catalyst under mild heating conditions (e.g., ambient to 55° C.), and adding an anti-solvent to the reaction mixture, thereby causing the statins in lactone form to crystalize from the reaction mixture. The acetic acid serves as both a solvent and a catalyst for the lactonization reaction.

11 Claims, No Drawings

PROCESS OF LACTONIZATION IN THE PREPARATION OF STATINS

BACKGROUND OF THE INVENTION

Lovastatin and its analogs, e.g., simvastatin, are potent antihyper-cholesterolemic agents that function by limiting cholesterol biosynthesis by inhibiting the enzyme HMG—CoA reductase. These compounds, which may be referred to generally as statins, are known to exist in open ring hydroxy acid and also in lactone form. The lactone form and the hydroxy acid form of these compounds have the following general structural Formulas:

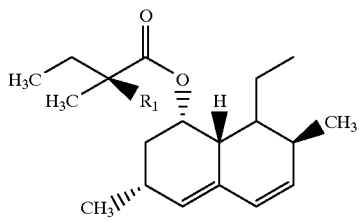

wherein Z is hydrogen, a metal cation, such as sodium or potassium, or $NH_4$, and R is

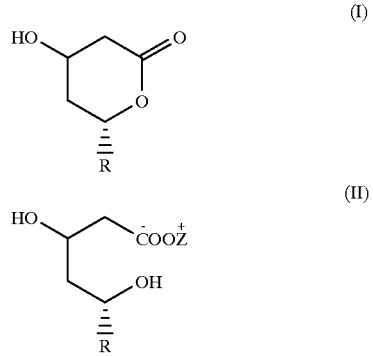

wherein $R_1$ is H or $CH_3$.

The open hydroxy acid form of the statins (Formula II) is the one which is biologically active. However, the statins are generally administered to a patient in the lactone form (Formula I), which is converted to its active metabolite, the hydroxy acid form, in the body.

In the process of manufacture of lovastatin and its analogs, e.g., simvastatin, the lactonization of free hydroxy acid or its salt to lactone form constitutes an essential step.

Processes known in the literature for the lactonization of the free, hydroxy acid or its salts are either carried out under drastic heat conditions, i.e., refluxing with inert solvents, or catalyzed by strong acids when lactonization is effected at ambient temperature. The process disclosed in U.S. Pat. No. 4,820,850 involves heating the free acid or its salt, e.g., the ammonium salt, to reflux temperature (usually 100–110° C.) in high boiling hydrocarbon solvents such as toluene for 7–8 hours. The ambient acidity of the acid is believed to be responsible for the lactonization reaction at these high temperatures. In addition, water which is formed as a by-product of the reaction is continuously removed by azeotropic distillation, which forces the reaction to near completion. The process of lactonization under heat conditions of reflux temperatures is complicated by the formation of many impurities, of which dimer formation especially lowers the quality of the final lactone product. The dimer is a difficult-to-remove impurity and is present at the levels of 0.4 to 0.8% in the product. In order to minimize the dimer impurity, high dilutions are often used in the lactonization reaction at the cost of the efficiency of the reaction and of the process, which is disadvantageous at a commercial manufacturing scale.

U.S. Pat. No. 4,916,239 discloses another process wherein the lactonization reaction is carried out at room temperature by treating the free hydroxy acid ammonium salt of a mevinic acid in a mixture of acetic acid and water, and in the presence of a strong acid catalyst. After the free hydroxy acid-lactone equilibrium is established (reaction has proceeded to 50% conversion), water is gradually added in lots to effect crystallization of the lactone from the reaction medium. This removal of lactone continuously shifts the equilibrium to the lactone side thus leading to reaction completion. This process suffers from several disadvantages and is also not convenient to operate at a large scale for a variety of reasons, some of which are discussed below Use of a strong mineral or an organic acid catalyst, e.g., formic, phosphoric, trifluoroacetic, sulphuric, hydrochloric, p-toluene sulphonic, methanesulphonic acids, etc., in quantities varying from 1.2 to 1.5 molar equivalents makes this process hazardous and environmentally unacceptable on an industrial scale. The excess acid catalyst which is used needs to be neutralized by adding a strong base before filtration of the product.

Furthermore, the lactonization reaction is only about 50% complete after the equilibrium is achieved. At this point of time, any fast or premature addition of water can lead to serious crystallization and filtration problems. Moreover, reaction and subsequent workup takes about 9–12 hours for completion, thereby decreasing the efficiency of the process.

The above-mentioned disadvantages make the process of U.S. Pat. No. 4,916,239 operationally tedious, inefficient, expensive and environmentally hazardous on an industrial scale.

SUMMARY AND DETAILED DESCRIPTION OF THE INVENTION

The aim of the present invention is to provide an efficient method for lactonization of statins which method avoids the use of strong corrosive acids and drastic heat conditions and gives a lactonized product of high purity and yield.

The present invention provides a novel process for converting the HMG—CoA reductase inhibitors, e.g., the open hydroxy acid forms of lovastatin, simvastatin, and analogs thereof, into their lactone forms, and is convenient to operate on an industrial scale. It allows the lactonizaion reaction to proceed at moderate temperatures without the use of industrially unsafe strong acids.

Specifically, the process of this invention comprises treating the open hydroxy acid of the statins, preferably in their salt form, most preferably in their ammonium salt form with acetic acid and in the absence of a strong acid catalyst, under inert anhydrous conditions and at ambient to moderate temperatures. (A strong acid is generally regarded as an acid having $pK_a<0$). Acetic acid with its mild acidic nature ($pK_a=4.8$) serves both as a solvent and as a catalyst, the catalytic property arising from its ambient acidity. The lactonization reaction proceeds without the addition of strong acid catalysts (as in the prior art), is clean and fast, thus allowing less chance for impurity formation. The lactonized product, generally having high solubility in acetic acid, is isolated in pure form after completion of reaction by the addition of an anti-solvent which has the ability to crystallize out the lactonized product. The anti-solvent is selected from water, hexane, heptane, cyclohexane, etc., preferably water, hexane or cyclohexane, most preferably, water.

Since lactonization is an equilibrium reaction, it is necessary to adopt some means to remove the reaction by-products (water and ammonia) to shift the equilibrium to the lactone side. Under the conditions selected for the present process, the reaction by-product ammonia is consumed in situ by the acetic acid, which is present in excess in the reaction medium, to generate ammonium acetate. The latter, being hygroscopic in nature, has a tendency to absorb water, which is also formed as a by-product during the lactonization reaction. There is, therefore, provided a mechanism which allows in situ removal of ammonia and water thereby driving the lactonization reaction to completion.

The lactonization reaction of the present invention can be represented as follows:

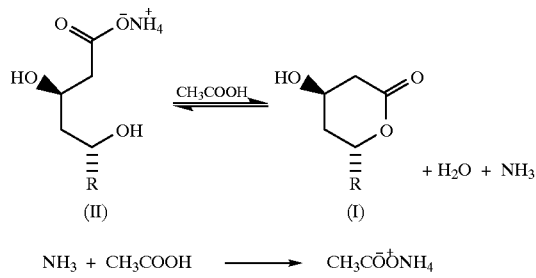

$$NH_3 + CH_3COOH \longrightarrow CH_3C\overset{-}{O}\overset{+}{O}NH_4$$

$$CH_3COONH_4 + H_2O \longrightarrow CH_3C\overset{-}{O}\overset{+}{O}NH_4 \cdot H_2O$$

wherein R is:

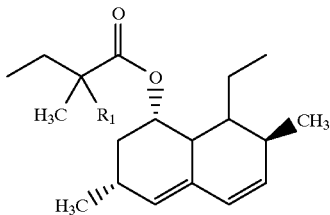

wherein $R_1$=H or $CH_3$.

The rate of lactonization is very high and allows the reaction to be completed in a very short period and the lactone product is obtained in high yields and high purity. Generally, the reaction is carried out at a temperature from ambient temperature to about 55° C., preferably at about 25–45° C., most preferably at about 35–40° C. The amount of acetic acid is at least about 1 part by volume per part of the starting salt material. Higher amounts of solvent and generally up to about 20 parts by volume may be used. Preferably, the solvent is in the range of about 3 to 7 parts by volume. The reaction will typically be accomplished within about 5–7 hrs. However, length of time will vary depending on such factors as total volume of solution, temperature of the reaction and the substrate involved.

Major advantages of the present invention as compared to the prior art procedures are cost effectiveness, less cumbersome workup, high yield, increased process productivity, clean and environmentally friendly operations.

The level of impurity profile, especially for the starting acid and the dimer, are greatly reduced as compared to earlier reported processes. The product which is in the form of a homogenous slurry makes the filtration operations at large scale very easy and workup involves no neutralization step prior to filtration.

The following specific examples illustrate the process of this invention, but they should not be construed as limiting the scope of this invention in any way.

EXAMPLE-1

Preparation of 6(R)-[2-[8(S)-(2-methylbutyryloxy)-2(S),6(R)-dimethyl-1,2,6,7,8,8a(R)-hexahydronaphthyl-1(S)]-ethyl]-4(R)-hydroxy-3,4,5,6-tetrahydro-2H-pyran-2-one (Formula I, $R_1$=H).

Ammonium-7-[1,2,6,7,8,8a(R)-hexahydro-2(S),6(R),dimethyl-8(S)-(2-methylbutyryloxy)-1(S)-naphthyl]-3(R),5(R)-dihydroxyheptanoate (Formula II, $R_1$=H) (4.5 g, 0.0102 moles) and butylated hydroxy toluene (15 mg) were dissolved in glacial acetic acid (27 ml) and stirred under nitrogen atmosphere for 5 hrs. at 35–38° C. After 5 hrs. when the reaction was nearly complete, water (64 ml) was added dropwise over 30 mins. at 30–32° C. The crystallized product was further stirred at this temperature for 30 mins. and then cooled to 15° C. The product was filtered and washed with water (15 ml×3) to remove the traces of acetic acid. Drying in vacuo at 40–42° C. afforded the title compound as a white crystalline material (3.82 g) in 92% yield and about 98% HPLC purity.

EXAMPLE-2

Preparation of 6(R)-[2-[8(S)-(2,2-dimethylbutyryloxy)-2(S),6(R)-dimethyl-1,2,6,7,8,8a(R)-hexahydronaphthyl-1 (S)]-ethyl]-4(R)-hydroxy-3,4,5,6-tetrahydro-2H-pyran-2-one (Formula I, $R_1$=$CH_3$).

Ammonium-7-[1,2,6,7,8,8a(R)-hexahydro-2(S),6(R)-dimethyl-8(S)-(2,2-dimethylbutyryloxy)-1(S)-naphthyl]-3(R),5(R)-dihydroxyheptanoate (Formula II, $R_1$=$CH_3$), (10 g, 0.022 moles, 97% purity by HPLC) and butylated hydroxy toluene (30 mg) were dissolved in glacial acetic acid (40 ml) and stirred under nitrogen atmosphere at 35–40° C. After 6 hrs., water (160 ml) was added to the reaction mixture over 30 mins. The crystallized lactonized product was further stirred at 30–32° C. for 60 mins. Filtration, washing with water (25 ml×3) and finally drying in vacuo at 40–42° C. afforded the title compound in white crystalline form (9.1 g) in >95% purity and >98% yield.

EXAMPLE-3

Preparation of 6(R)-[2-[8(S)-(2,2-dimehylbutyryloxy)-2(S),6(R)-dimethyl-1,2,6,7,8,8a(R)-hexahydronaphthyl-1(S)]-ethyl]-4(R)-hydroxy-3,4,5,6-tetrahydro-2H-pyran-2-one (Formula I, $R_1$=$CH_3$).

Ammonium-7-[1,2,6,7,8,8a(R)-hexahydro-2(S),6(R)-dimethyl-8(S)-(2,2-dimethylbutyryloxy)-1(S)-naphthyl]-3(R),5(R)-dihydroxyheptanoate (Formula II, $R_1$=$CH_3$) (2 g, 0.004 moles, 95% purity by HPLC) and butylated hydroxy toluene (6 mg) were dissolved in acetic acid (6 ml). The mixture was stirred under nitrogen at 35–40° C. for 5 hrs and then hexane (130 ml) was slowly added to crystallize out the product. The reaction mixture was further stirred for 60 mins. at 30–32° C. Filtration, washing with hexane (5 ml×2) and drying in vacuo at 40–42° C. gave the title compound in crystalline form (1.75 g, 95% yield) and >95% purity.

EXAMPLE-4

Preparation of 6(R)-[2-[8(S)-(2,2-dimethylbutyryloxy)-2(S),6(R)-dimethyl-1,2,6,7,8,8a(R)-hexahydronaphthyl-1(S)]-ethyl]-4(R)-hydroxy-3,4,5,6-tetrahydro-2H-pyran-2-one Formula I, $R_1=CH_3$).

Adopting the same procedure as in Example-3 but substituting cyclohexane as an anti-solvent, the title compound was obtained in crystalline form in about 87% yield and >97% purity.

EXAMPLE-5

Preparation of 6(R)-[2-[8(S)-2(methylbutyryloxy)-2(S),6(R)-dimethyl-1,2,6,7,8,8a(R)-hexahydronaphthyl-1(S)]-ethyl]-4(R)-hydroxy-3,4,5,6-tetrahydro-2H-pyran-2-one (Formula I, $R_1=H$).

Adopting the same procedure as in Example-1 but substituting cyclohexane as an anti-solvent, the title compound was obtained in crystalline form in 85% yield and >98% purity.

What is claimed is:

1. A process for the manufacture of a compound of Formula I:

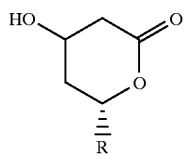

(I)

wherein R is:

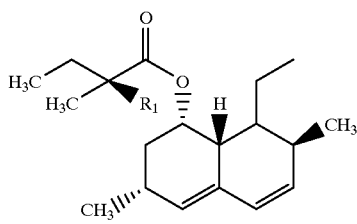

wherein $R_1$ is H or $CH_3$, which comprises treating a compound of Formula II:

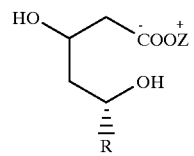

(II)

wherein Z is hydrogen, a metal cation, or $NH_4$, and wherein R is as defined above, with a weak organic acid and in the absence of a strong acid at a temperature below about 55° C., to form a reaction mixture and recovering said compound of Formula I, from said reaction mixture.

2. The process of claim 1 wherein said weak organic acid is acetic acid.

3. The process of claim 1 further comprising adding an anti-solvent to said reaction mixture, thereby causing said compound of Formula I to precipitate from said reaction mixture.

4. The process of claim 3 wherein said compound of Formula I is precipated from said reaction mixture as a crystalline product.

5. The process of claim 3 wherein said anti-solvent is water, hexane, heptane, or cyclohexane.

6. The process of claim 3 wherein said anti-solvent is water.

7. The process of claim 1 wherein Z is Na, K, or $NH_4$.

8. The process of claim 1 wherein Z is $NH_4$.

9. The process of claim 1 which is carried out at a temperature of about 25–45° C.

10. The process of claim 1 which is carried out at a temperature of about 35–40° C.

11. The process of claim 1 which is carried out for a period of about 5–7 hours.

* * * * *